United States Patent [19]

Adams

[11] 4,432,240
[45] Feb. 21, 1984

[54] ELASTOMERIC TESTING APPARATUS

[75] Inventor: John O. Adams, Madisonville, Tenn.

[73] Assignee: Olin Corporation, New Haven, Conn.

[21] Appl. No.: 345,171

[22] Filed: Feb. 2, 1982

[51] Int. Cl.³ ............................................. G01N 3/08
[52] U.S. Cl. .................................................... 73/822
[58] Field of Search ................. 73/822, 818, 819, 820, 73/821, 823, 824, 825

[56] References Cited

U.S. PATENT DOCUMENTS

| | | | |
|---|---|---|---|
| 1,145,924 | 7/1915 | Russell | 73/819 |
| 2,082,364 | 6/1937 | Store | 73/818 |
| 2,482,147 | 9/1949 | Bashore | 73/823 |
| 2,637,203 | 5/1953 | Gehman | 73/825 |
| 2,810,289 | 10/1957 | Button | 73/823 |
| 3,214,961 | 11/1965 | Brown et al. | 73/822 |
| 3,887,022 | 6/1975 | Stanev | 73/862.62 |

FOREIGN PATENT DOCUMENTS 2529491  1/1977  Fed. Rep. of Germany ........ 73/818

*Primary Examiner*—Jerry W. Myracle
*Attorney, Agent, or Firm*—Ralph D'Alessandro; Donald F. Clements; Thomas P. O'Day

[57] ABSTRACT

In an apparatus for determining the amount of compressive force exerted on an elastomeric material, there is provided an elastomeric material retainer, compression apparatus cooperative with the elastomeric material retainer and compressive force measuring apparatus and deflection apparatus to measure the amount of compressive force exerted on the elastomeric material and the amount of compression which the elastomeric material experiences.

8 Claims, 3 Drawing Figures

ELASTOMERIC TESTING APPARATUS

BACKGROUND OF THE INVENTION

The present invention relates generally to a pressure applying device and more specifically relates to a device for measuring the amount of compressive force that is applied to elastomeric material, such as gaskets.

With the advent of filter press membrane electrolytic cells for the production of chlorine in alkali metal hydroxides, there has been increased attention given to efficient manufacture and assembly of components that comprise chlor-alkali cells. The development of separators that have ion-exchange properties, such as the membranes marketed by E. I. DuPont de Nemours & Co. under the trademark Nafion ® and by Asahi Glass Company under the trademark Flemion ®, have heightened the interest in the filter press type of cell. These cells are generally assembled so that they stand vertically and have alternately positioned cathodes and anodes, separated by the membranes, which are compressed together in a fluid-tight arrangement by hydraulic stud tensioners or other mechanical compression assembly apparatus.

In order to effect this fluid-tight sealing, means, such as elastomeric gaskets, have been employed between each electrode and the intervening membrane in an attempt to both effect the fluid-tight seal and to prevent damage to the membrane. One of the problems encountered with this type of assembly lies in the proper selection of gaskets which deform uniformly without excessive pressure to effect the fluid-tight seal. The need to effect compression without excessive pressure is important to prevent potential damage from occuring to the membrane separators between the electrodes, as well as to ensure that warping or failure of the electrode frames themselves does not occur.

Since the gaskets employed in the assembly of filter press cells are obtained from a number of suppliers, there is frequently substantial difference between one manufacturer's product and another's product, as well as a difference between the products supplied from the same manufacturer. The difference in the quality of the gaskets of allegedly the same durometer normally was not discovered until the cell was assembled and filled with electrolyte fluid. Thus, when a problem was discovered, the cell had been placed in an operating condition and the electrolyte fluid was found to leak due to faulty gaskets. To correct the situation, a filter press type of cell would then have to be drained of its electrolyte fluids and disassembled. All of this, naturally, was time-consuming and wasteful of effort.

Thus, there is a need to establish whether a gasket is suitable for use within a filter press type of cell prior to actual incorporation into its assembled unit. Additionally, there is a need to check for defective gaskets and to establish the exact amount of pressure that must be effected by the exertion of compressive forces against the electrode frames in order to compress the rubber gasket material to the desired degree. It has been found that pressure within the range of 600 to 700 pounds per square inch is optimum to reduce the potential for damage to the membrane separators, as well as to compress the rubber gaskets about 30 to 35% of their original thickness. This percent compression has been found to be the optimum range of compression recommended by the gasket manufacturers to effect uniform fluid-tight sealing and optimum gasket performance. Heretofore, there has been no convenient way to pretest the gaskets to be employed in the assembly of a filter press type of cell prior to assembly.

It is to be understood that the term compression as used heretofore and as will be used hereafter includes the concept of deformation, especially when applied to use in conjunction with gaskets. The gaskets, when compressed, actually deform in response to the compressive forces, expanding or deforming in the unrestrained directions.

These problems are solved in the design of the apparatus comprising the present invention by providing a device for determining the amount of a compressive force exerted on elastomeric material, such as a gasket, and the amount of compression experienced by the tested material prior to its insertion in a filter press membrane electrolytic cell.

SUMMARY OF THE INVENTION

It is an object of the present invention to provide an apparatus that will permit a compression test to be performed on elastomeric materials that are incorporated into assembled filter press membrane electrolytic cells prior to assembly.

It is another object of the present invention to provide a simple and low cost device that may be employed to detect defective or undesirable elastomeric materials prior to incorporation into an assembled filter press membrane electrolytic cell.

It is a feature of the present invention that an elastomeric material retainer is employed within which an elastomeric material, such as a gasket, may be placed and subjected to compressive forces.

It is another feature of the present invention that the bottom surface of the elastomeric material retainer can be either grooved or flat to match the surface that is encountered on the electrode frame.

It is another feature of the present invention that a force gauge is employed on the apparatus to measure the force that is applied to the elastomeric material.

It is a further feature of the present invention that a dial indicator can be employed to measure the deformation that occurs in an elastomeric material, such as a gasket, during a compression test.

It is an advantage of the present invention that an elastomeric material may be tested prior to its incorporation into a filter press membrane electrolytic cell, thereby providing a means of testing the elastomeric material prior to assembling the cell.

It is another advantage of the present invention that it can be determined before assembly of the filter press membrane electrolytic cell whether the elastomeric material, such as a gasket, will require pressure beyond that range that is safe to use in conjunction with ion-exchange membranes to achieve compression levels that will effect a fluid-tight seal between the electrode frames.

It is another advantage of the present invention that the elastomeric materials, such as gaskets, can be compressed within the force limits that would be exerted by hydraulic or other mechanical compression assembly apparatus.

It is another advantage of the present invention that there is the ability to test the amount of compressive force that is required to achieve the desired amount of deformation with elastomeric gasket material either retained or partially retained on two sides, but not retained on the other two sides to thereby simulate the forces to which a gasket is subjected during its use in a filter press membrane electrolytic cell.

These and other objects, features, and advantages are obtained in an apparatus for determining the amount of compressive force exerted on an elastomeric material which comprises an elastomeric material retainer, compressive force measuring means to measure the amount of compressive force that is selectively exerted on elastomeric material.

BRIEF DESCRIPTION OF THE DRAWINGS

The advantages of this invention will become apparent upon consideration of the following detailed description of the disclosure, especially when it is taken in conjunction with the accompanying drawings wherein.

DETAILED DESCRIPTION OF THE PREFERRED EMBODIMENT

Figures 1, 2, 3:
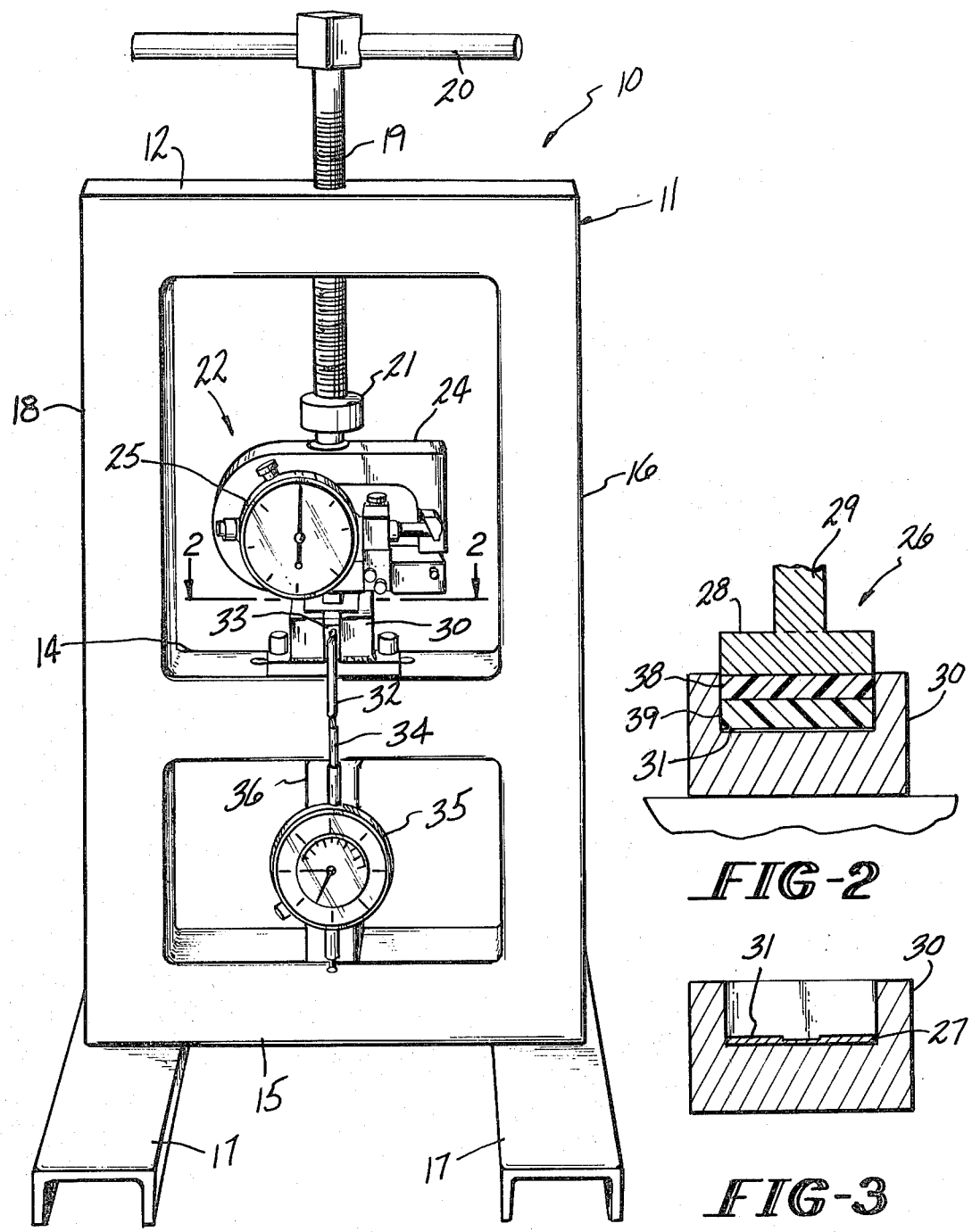
FIG. 1 is a front perspective view of the apparatus.
FIG. 2 is an enlarged rear sectional view taken along the line 2—2 of FIG. 1 through the elastomeric material retainer and the foot of the compressive force measuring means showing the compressive force being exerted on a pair of gaskets.
FIG. 3 is an enlarged rear sectional view taken through the elastomeric material retainer showing a grooved bottom surface insert.

Referring now to FIG. 1, there is shown the apparatus, indicated generally by the numeral 10, which is used to compress the elastomeric material. Apparatus 10 comprises a frame, indicated generally by the numeral 11, which is formed of horizontal members 12, 14, and 15 and two vertical members 16 and 18. A press screw 19 has a handle 20 on its topmost portion and fits through an appropriately sized threaded aperture (not shown) in horizontal member 12. Frame 11 is appropriately affixed to channel stand members 17 to provide a stable base for the apparatus 10. A brass retainer 21 is affixed to the bottom of press screw 19 and is detachably connected via an appropriately sized recess to a compressive force measuring means indicated generally by the numeral 22.

Compressive force measuring means or force gauge 22 has a substantially closed top generally U-shaped member 24 that lies on its side and has a gauge 25 connected thereto so that it can record the amount of force exerted on the elastomeric material to be tested. This compressive force measuring means 22 has a foot 26 that extends out from the bottom-most portion of the U-shaped member. Foot 26, best seen in FIG. 2, is comprised of a flat plate 28 that is attached to a threaded rod 29.

Appropriately fastened to the horizontal member 14 of frame 11 is the elastomeric material retainer 30. The retainer 30 is an elongate, generally rectilinear retainer having a hollowed out central area with a bottom surface 31 best seen in FIGS. 2 and 3. This surface can either be flat as seen in FIG. 2, or can be grooved, by the insertion of a bottom surface insert 27, as seen in FIG. 3, to duplicate the contour of the electrode channels against which elastomeric gaskets are placed during the assembly of a filter press membrane electrolytic cell. The retainer 30 is slotted on its front side to receive a deflector arm 32, seen in FIG. 1.

Deflector arm 32 is connected to the foot 26 of compressive force measuring means 22, such as by welding or by a threaded connection to allow it to be removed.

Deflector arm 32 extends out the front of retainer 30 through the slot 33 of FIG. 1 and is bent 90° downwardly. Deflector arm 32 contacts a deflector dial lead-in 34 that transmits the compression of the elastomeric material within the retainer 30 to its deflector dial indicator 35 when compressive force is applied by tightening the press screw 19. Deflector dial indicator 35 is mounted to a vertical member 36 that extends between bottom horizontal member 15 and intermediate horizontal member 14. This compression or deformation of the elastomeric material is measured by zeroing the deflector dial indicator 35 at the point where the bottom of the flat plate 28 that is attached to the threaded rod 29 just touches the elastomeric material that is to be compressed within the elastomeric material retainer 30.

The compressive force measuring means 22 has been described only generally because it is old and well known in the art. It is available commercially as a Dillon force gauge from the Dillon Co. of Van Nuys, Calif. This gauge can read applied force up to 1,200 pounds. Similarly, the deflector dial indicator 35 has been described only generally, but is available commercially as a Mitutoyo dial indicator that will measure deflection from 0.001 inches to 0.50 inches as a measure of gasket or elastomeric material deformation.

In operation, an elastomeric material, such as the gaskets 38 and 39 shown in FIG. 2, are cut to the exact length of the inside length of the elastomeric material retainer 30 and to any desired width. Typically, 1 inch long or 2 inch long samples have been used. The press screw 19 is loosened by turning the handle 20 in the appropriate direction to raise the compressive force measuring means 22 and its foot 26 out of the elastomeric material retainer 30. The gaskets 38 and 39 are then inserted in the retainer 30 as seen in FIG. 2. A piece of membrane material (not shown) can be inserted between the gaskets 38 and 39 to simulate the exact conditions which occur during the assembly of a filter press membrane electrolytic cell. It should be noted that a single layer of elastomeric material, such as an O-ring or a gasket, could be satisfactorily tested. The press screw is then turned in the opposing direction and the compressive force measuring means 22 with its foot 26 is lowered until the foot 26 is in contact with the elastomeric material. The dial indicator 35 is zeroed at this time.

The test is now performed by turning the press screw 19 to cause the foot 26 to press against the elastomeric material. This compressive force is transferred through the foot 26 to the elastomeric material which causes a reading, generally in pounds, to be registered on the gauge 25. Deflector arm 32 measures the amount of compression or deformation that is experienced by the elastomeric material in terms of deflection and transmits this deflection to the dial indicator 35 which gives a reading in inches. The compressive force is gradually increased, generally in increments of 100 pounds, and the corresponding deflection is read at each increment. To permit the gasket material to settle or to allow for gasket "creep" at each increment of compressive force, the gauge 25 reading is allowed to stabilize before any force or deflection readings are taken. This can take as long as two to five minutes at each increment of compressive force applied.

Thus, elastomeric materials, such as gaskets or O-rings may be pretested for their performance characteristics to ensure their fitness for the purpose for which they will be employed within a filter press membrane electrolytic cell. Should the gaskets, for example, require more force to achieve the optimum 30-35% compression than can safely be exerted on the ion exchange membrane separators without causing tearing or other damage, the gaskets can be replaced prior to their being included in an assembled cell. Similarly, gaskets which cannot be compressed sufficiently within the desired force range to effect fluid-tight seals can also be determined prior to inclusion in a cell.

It should be noted that by cutting, for example, the gaskets to the exact length of the inside length of the elastomeric material retainer 30, the gaskets are retained on two sides. Since the width of the gaskets are less than the width of the elastomeric material retainer 30, the gasket may deform outwardly along its two unrestrained sides in response to the application of compressive force through the press screw 19.

While the preferred structure in which the principles of the present invention have been incorporated is shown and described above it is to be understood that the invention is not to be limited to the particular details thus presented, but in fact, widely different means may be employed in the practice of the broader aspects of this invention. The scope of the appended claims is intended to encompass all obvious changes in the details, materials and arrangement of parts which will occur to one of skill in the art upon a reading of the disclosure.

Having thus described the invention, what is claimed is:

1. Apparatus for determining the amount of compressive force exerted on an elastomeric material of generally rectangular configuration; comprising in combination:
   a. a frame;
   b. an elongate generally rectilinear elastomeric material retainer connected to the frame having a hollowed out central area adapted to receive and retain at least partially along two sides the elastomeric material during compression;
   c. compression means connected to the frame cooperative with the elastomeric material retainer effective to selectively exert a predetermined amount of compressive force on the elastomeric material;
   d. compressive force measuring means connected to the frame having a pressure plate contactable with the elastomeric material and cooperative with the elastomeric material retainer to measure the amount of compressive force exerted on the elastomeric material; and
   e. deflection measuring means mounted to the frame including a deflector arm and cooperative with the elastomeric material retainer and the elastomeric material to measure the amount of compression which the elastomeric material experiences as a function of the deflector arm in response to the selective exertion of compressive force, the amount of compression being transmitted as a deflection through the deflector arm.

2. The apparatus according to claim 1 wherein the compression means further comprises a threaded press screw with a first end and an opposing second end, the first end further having a handle attached thereto to assist in exerting compressive force by turning the press screw in a predetermined direction and the second end being connected to the compressive force measuring means.

3. The apparatus according to claim 2 wherein the compressive force measuring means further comprises a force gauge.

4. The apparatus according to claim 3 wherein the compressive force measuring means further comprises a substantially closed topped, generally U-shaped member with a pressure plate extending from its lower-most portion to contact the elastomeric material and transmit the compressive force exerted by the threaded press screw thereto.

5. The apparatus according to claim 4 wherein the deflection measuring means further comprises a dial indicator cooperative with the deflector arm for measuring the amount of compression which the elastomeric material experiences as a function of the deflector arm.

6. The apparatus according to claim 1 wherein the hollowed out central area of the elastomeric material retainer further comprises a bottom surface.

7. The apparatus according to claim 6 wherein the bottom surface is flat.

8. The apparatus according to claim 6 wherein the bottom surface is grooved.

* * * * *